US012576282B2

(12) United States Patent
Pang et al.

(10) Patent No.: US 12,576,282 B2
(45) Date of Patent: Mar. 17, 2026

(54) WEARABLE PHOTOTHERAPY DISPLAY DEVICE

(71) Applicant: BEIJING SUMMER SPROUT TECHNOLOGY CO., LTD., Beijing (CN)

(72) Inventors: Huiqing Pang, Beijing (CN); Paul Edward Burrows, Beijing (CN)

(73) Assignee: Beijing Summer Sprout Technology Co., LTD., Beijing (CN)

( * ) Notice: Subject to any disclaimer, the term of this patent is extended or adjusted under 35 U.S.C. 154(b) by 397 days.

(21) Appl. No.: 18/304,058

(22) Filed: Apr. 20, 2023

(65) Prior Publication Data

US 2023/0338742 A1 Oct. 26, 2023

(30) Foreign Application Priority Data

Apr. 21, 2022 (CN) .......................... 202210413463.5

(51) Int. Cl.
*A61N 5/06* (2006.01)

(52) U.S. Cl.
CPC ........ *A61N 5/06* (2013.01); *A61N 2005/0648* (2013.01); *A61N 2005/0653* (2013.01); *A61N 2005/0659* (2013.01); *A61N 2005/0663* (2013.01)

(58) Field of Classification Search
CPC .... A61N 2005/0648; A61N 2005/0653; A61N 2005/0659; A61N 2005/0663; A61N 5/0616; A61N 2005/0662; A61N 2005/0647; A61N 5/06–2005/073
See application file for complete search history.

(56) References Cited

U.S. PATENT DOCUMENTS

| | | | | |
|---|---|---|---|---|
| 10,224,515 B2 * | 3/2019 | Lim | ...................... | H10K 59/12 |
| 11,247,021 B2 * | 2/2022 | Levenberg | ........... | G06V 40/171 |
| 11,552,278 B2 * | 1/2023 | Hack | ................... | H10K 59/351 |

(Continued)

FOREIGN PATENT DOCUMENTS

| | | |
|---|---|---|
| CN | 208511681 U | 2/2019 |
| CN | 208750423 U | 4/2019 |

(Continued)

OTHER PUBLICATIONS

Chan Hee Nam et al., The Efficacy and Safety of 660 nm and 411 to 777 nm Light-Emitting Devices for Treating Wrinkles, Dermatologic Surgery, 2017, 43:371-380, DOI: 10.1097/DSS.0000000000000981 (10 pages).

(Continued)

*Primary Examiner* — Jonathan T Kuo
(74) *Attorney, Agent, or Firm* — Sandberg Phoenix & von Gontard, PC

(57) ABSTRACT

A wearable phototherapy display device comprises a display unit and a light source; wherein the display unit has an imaging plane, and the imaging plane is disposed directly in front of the human eye; the light source emits light having a peak wavelength between 400 nm and 1400 nm, and the light emitted by the light source is directed towards at least a part of a periocular region; the light source comprises a light-emitting surface, and the included angle between the light-emitting surface and the imaging plane is less than 30 degrees.

22 Claims, 11 Drawing Sheets

(56)  References Cited

U.S. PATENT DOCUMENTS

| | | | |
|---|---|---|---|
| 2013/0041432 A1* | 2/2013 | Tucker | A61N 5/0617 |
| | | | 607/90 |
| 2016/0067087 A1* | 3/2016 | Tedford | A61N 5/0624 |
| | | | 606/4 |
| 2017/0084867 A1* | 3/2017 | Lim | H10K 59/873 |
| 2019/0348628 A1* | 11/2019 | Hack | H10K 59/351 |
| 2019/0376650 A1 | 12/2019 | Pang et al. | |
| 2020/0188629 A1* | 6/2020 | Levenberg | A61N 1/3603 |
| 2021/0119162 A1 | 4/2021 | Gao et al. | |
| 2022/0054854 A1* | 2/2022 | Zheng | A61N 5/06 |
| 2022/0072333 A1* | 3/2022 | Lin | A61N 5/0613 |

FOREIGN PATENT DOCUMENTS

| CN | 111081891 A | 4/2020 |
|---|---|---|
| CN | 111081892 A | 4/2020 |
| CN | 111538171 A | 8/2020 |
| CN | 112687811 A | 4/2021 |

OTHER PUBLICATIONS

Daniel Barolet, Light-Emitting Diodes (LEDs) in Dermatology, Seminars in Cutaneous Medicine and Surgery, 2008, 27:227-238 (12 pages) doi:10.1016/j.sder.2008.08.003.

Yongmin Jeon, et al., A Wearable Photobiomodulation Patch Using a Flexible Red-Wavelength OLED and Its In Vitro Differential Cell Proliferation Effects, Advanced Materials Technology, 2018, 1700391-1700391 (10 pages) ; DOI: 10.1002/admt.201700391.

Michael R. Hamblin, Ying-ying Huang, Handbook of Photomedicine, Chapter 22 "Recent Advances in Developing Improved Agents for Photodynamic Therapy"; CRC Press, taylor & Francis Group; 2014; 53 pages total.

Website: https://noctura.com/, 6 pages, accessed Apr. 17, 2023.

Kun Li, Understanding Waveguide: the Key Technology for Augmented Reality Near-eye Display (Part II) (2019), https://arvrjourney.com/understanding-waveguide-the-key-technology-for-augmented-reality-near-eye-display-part-ii-fe4bf3490fa, accessed Apr. 18, 2023.

* cited by examiner

100

110
109
108
107
106
105
104
103
102
101

200

205
204
203
202
201

1

WEARABLE PHOTOTHERAPY DISPLAY DEVICE

CROSS-REFERENCE TO RELATED APPLICATION(S)

This application claims priority to a Chinese patent application No. 202210413463.5 filed on Apr. 21, 2022, disclosure of which is incorporated herein by reference in its entirety.

TECHNICAL FIELD

The present disclosure relates to the field of display technology and specifically, to a wearable phototherapy display device having a phototherapy effect.

BACKGROUND

Technologies such as low-light laser treatment and photobiomodulation (PBM) emerged in the middle and late 20th century and had been applied to the medical field using light as a means of disease treatment (Michael R. Hamblin, Ying-ying Huang, *Handbook of Photomedicine*, CRC Press). Various studies in recent years have shown that red light to near-infrared light can help to promote the regeneration of tissues such as collagen and skin cells and can be applied in the fields such as anti-wrinkle and cosmetic treatment, wound healing, and spot and scar removal (Chan Hee Nam et al., *Dermatologic Surgery*, 2017, 43:371-380; Daniel Barolet, Semin Cutan Med Surg, 2008, 27:227-238; Yongmin Jeon, *Adv. Mater. Technol.* 2018, 1700391). In vitro studies have shown that the spectral regions of visible light to near-infrared light can stimulate the synthesis of skin collagen. In addition, red light therapy is a useful tool to reduce redness and swelling and mediate inflammation and especially helps to slow signs of aging. Specific red light wavelengths can target the deep layers of the skin and help to promote the regeneration of tissues such as collagen and skin cells. Red light can not only mediate inflammation on the surface of the skin, but also mediate inflammation in the deeper layers of the skin. Different wavelengths have different chromophores and have different effects on tissues. The use of wavelengths usually refers to the use of colors of light associated with these wavelengths, including blue, green, red, and near-infrared light. Generally, the longer the wavelength, the deeper the light penetrates into tissues. FIG. 2A shows the penetration depth of light of different wavelengths into the skin tissue. As can be seen, light having a wavelength of 600 nm to 1000 nm can penetrate into the dermis to a depth of 2 mm to 4 mm below the skin (Daniel Barolet, *Semin Cutan Med Surg,* 2008, 27:227-238). In addition to the penetration depth, the absorption of light by cell tissues must also be taken into account for determining the effective wavelength of the phototherapy light source. At the wavelength of 600 nm, blood hemoglobin (Hb) is a major obstacle to photon absorption, and further, at the wavelength of 1000 nm, the light absorption of water begins to become very strong. FIG. 2B shows the absorption of light of different wavelengths of different physiological substances (such as water, hemoglobin, oxyhemoglobin, and melanin). As can be seen, the best wavelength window of light that can penetrate into the skin tissue without loss is roughly between 600 nm and 1400 nm (Daniel Barolet, *Semin Cutan Med Surg,* 2008, 27:227-238). According to the relationship between wavelengths and penetration depths, red light and near-infrared light of wavelengths of 600 nm to 1000 nm are the best choices for non-invasive phototherapy. Moreover, recent studies have shown that green light can treat eye diseases caused by diabetes, and eye masks using such green light have been available on the market (noctura.com).

The concept of virtual reality (VR) was born in the 1950s. With the development of VR technology, VR has gradually expanded from military use to civil use and has evolved from heavy helmets to today's head-mounted glasses. At present, people can wear VR glasses to watch movies and play games, and the VR glasses are popular with consumers because of the more realistic immersive experience they bring. In another aspect, augmented reality (AR) glasses can increase the interaction between the virtual world and the real world and have also been rapidly developed like VR products. The imaging of the VR head-mounted glasses is generally achieved in two methods. In one of the methods, two micron display units are used, each of which is disposed in front of the human eye, sometimes with some optical lenses added, to directly form images in front of the human eye. In the other method, one micron display unit is disposed on each of two sides of the human face, and then formed images are transferred in front of the human eye through optical waveguide lenses for imaging. The imaging principle is shown in FIG. 2C (arvrjourney.com). The latter method reduces the use of optical lenses, and since the optical waveguide lens is generally transparent, the AR glasses are more likely to be produced and this method becomes a more potential solution. Predictably, the development of VR and AR products will become better and better in the future. Therefore, there is an intuitive idea to carry out phototherapy on the eyes and their surrounding regions during the use of VR/AR glasses to further enhance the functionality and practicability of these electronic devices.

Patent CN208511681U discloses a VR head-mounted device for improving sleep quality, including a phototherapy assembly disposed around an optical lens. First, the patent only discloses that the phototherapy assembly is disposed at the periphery of the optical lens, and further discloses that the phototherapy assembly is disposed below and/or above or on two sides of the optical lens. The patent does not mention the light-emitting surface of the light source and the relationship between the imaging plane and the light-emitting surface. According to the embodiments and drawings disclosed in this patent, the phototherapy assembly includes two LED light sources that are each disposed around the optical lens respectively to emit light to the pupils of two eyes. Those skilled in the art know that the two LED light sources in this application cannot form a light-emitting surface, and this case is quite different from the present disclosure. The light source in the wearable phototherapy display device of the present disclosure cannot be arbitrarily integrated around the optical lens, the light-emitting surface of the light source must be rationally arranged according to the characteristics of the imaging plane, the included angle between the light-emitting surface of the light source and the imaging plane is less than 30 degrees, and the light-emitting surface is roughly parallel to the imaging plane so that the phototherapy can be better carried out without affecting the display. Second, in this patent, light having specific wavelengths is emitted by the phototherapy assembly to stimulate the suprachiasmatic nucleus in the hypothalamus to regulate the secretion levels of cortisol and melatonin at different time periods, so as to improve sleep quality. Therefore, the light emitted by the phototherapy assembly must be directed at the eyes to stimulate the hypothalamus for treatment. This patent further discloses that the phototherapy assembly emits blue light. Obviously, irradiating the eyes with blue light will interfere with the contents displayed on the VR display screen so that the functions of display and photo-therapy cannot be achieved simultaneously. The wearable phototherapy display device of the present disclosure mainly carries out phototherapy on the skin in the periocular region, and may simultaneously achieve the functions of display and phototherapy.

SUMMARY

The present disclosure aims to provide a wearable pho-totherapy display device having a phototherapy effect to solve at least part of the above problems.

According to an embodiment of the present disclosure, disclosed is a wearable phototherapy display device, which includes:

a display unit and a light source.

wherein the display unit has an imaging plane, and the imaging plane is disposed directly in front of the human eye;

the light source emits light having a peak wavelength between 400 nm and 1400 nm, and the light emitted by the light source is directed towards at least a part of a periocular region; and the light source comprises a light-emitting surface, and an included angle between the light-emitting surface and the imaging plane is less than 30 degrees.

The present disclosure discloses a wearable phototherapy display device including a display unit and a light source. The display unit has an imaging plane, the imaging plane is disposed directly in front of the human eye, the light source emits light having a peak wavelength between 400 nm and 1400 nm, and the emitted light is directed towards at least a part of the periocular region. The light source includes a light-emitting surface, and the included angle between the light-emitting surface and the imaging plane is less than 30 degrees. Such a wearable phototherapy display device enables people to receive phototherapy at the periocular region or on the eyes when people are watching a movie, playing a game or carrying out other virtual work, and the light-emitting surface of the wearable phototherapy display device can better carry out phototherapy at the periocular region or on the eyes without affecting display, thereby achieving multiple purposes and enhancing the functionality and practicality of these electronic devices.

DETAILED DESCRIPTION

Figure 1A:
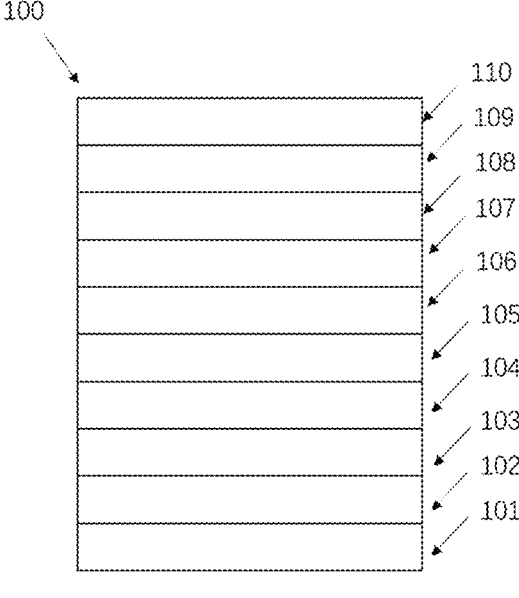
FIG. 1A is a structure diagram of a single-layer OLED device.

As used herein, "top" refers to being the farthest from a substrate, and "bottom" refers to being the closest to the substrate. Where a first layer is described as "disposed on" a second layer, the first layer is disposed further away from the substrate. Otherwise, where the first layer is described as "disposed below" the second layer, the first layer is disposed closer to the substrate. There may be other layers between the first and second layers, unless it is specified that the first layer is "in contact with" the second layer. For example, a cathode may be described as "disposed on" an anode, even though there are various organic layers in between.

As used herein, the term "OLED device (OLED unit)" includes an anode layer, a cathode layer, and one or more organic layers disposed between the anode layer and the cathode layer. An "OLED device (OLED unit)" may be a bottom-emission (bottom-emitting) device, that is, it emits light from a side of the anode, or the "OLED device (OLED unit)" may be a top-emission (top-emitting) device, that is, it emits light from a side of the cathode, or the "OLED device (OLED unit)" may be a double-sided light-emitting device, that is, it emits light from the side of the anode and the side of the cathode simultaneously.

As used herein, the term "encapsulation layer" may be a thin-film encapsulation with a thickness of less than 100 micrometers, which includes one or more thin films directly arranged on the device, or the "encapsulation layer" may be a cover glass adhered to the substrate.

As used herein, the term "effective light-emitting area" refers to the portion of the planar area where the anode, organic layers and cathode overlap or the portion of the planar area where the charge generation layer, organic layers and cathode overlap, and does not include the light extrac-tion effect.

As used herein, the term "light-emitting surface" refers to the surface from which the light source emits light. For example, if the light source includes a bottom-emitting OLED light-emitting panel, the "light-emitting surface" is the surface that includes the substrate away from the anode, and if the "light-emitting surface" is the top-emitting device, the "light-emitting surface" is the surface that includes the encapsulation layer away from the cathode. It is to be noted that when the light source is a flexible light source, the "light-emitting surface" may include a curved surface. If the light source is an LED lamp bead, it can only form a light-emitting point because it is a point light source; however, in a special circumstance, if three or more LED lamp beads are arranged in a plane without forming a straight line, the plane where the series of LED lamp beads are located is considered as a "light-emitting surface".

The term "light-emitting region of an OLED light source" refers to the portion of the planar area where the anode, organic layers and cathode overlap, or the portion of the planar area where the charge generation layer, organic layers and cathode overlap, and various light extraction effects.

As used herein, the term "single-layer device" refers to a device having one light-emitting layer (or multiple successive light-emitting layers) between a pair of anode and cathode and a single set of hole and electron transport layers matched therewith. That is, such a device having a single light-emitting layer (or multiple successive light-emitting layers) and matched transport layers thereof is the "single-layer device".

As used herein, the term "stacked device" refers to a device having multiple light-emitting layers between a pair of anode and cathode, where each light-emitting layer has its own independent hole transport layer and electron transport layer, each light-emitting layer and its matched hole transport layer and electron transport layer constitute a light-emitting sub-unit, and these light-emitting sub-units are connected to each other through charge generation layers. That is, the device having multiple such light-emitting sub-units is the "stacked device".

As used herein, the term "imaging plane" refers to a plane that is displayed by a display unit and forms images in front of the human eye, which may be the display screen plane of the display unit itself or a plane forming images in a region other than the display screen using an optical element (for example, an optical lens). It is to be noted that when the image displayed by the display unit is formed through the optical lens having a radian, the "imaging plane" is between the optical lens and the human eye at this point, but the formed image is still on a plane, so there is still an "imaging plane". It can be assumed that if a piece of white paper is placed between the optical lens and the human eye (without affecting the formed image) and moves between the optical lens and the human eye, when a complete image is displayed on the white paper, the plane where the white paper is located is the "imaging plane". As for the wearable phototherapy display device in the present application, when the micron display unit is disposed on a side of the human face, the formed image can be transferred in front of the human eye for imaging through an optical waveguide lens, imaging is carried out between the optical waveguide lens and the human eye at this point, and the plane where the image is formed is the "imaging plane"; when the micron display unit is disposed directly in front of the human eye, the imaging plane may be the display screen plane of the micron display unit; when some optical lenses are disposed directly in front of the micron display unit, imaging is carried out between the optical lenses and the human eye at this point, and the plane where the image is formed is the "imaging plane".

As used herein, the term "imaging" refers to displaying a unique image by the display unit, where the image may be single-colored or full-color but must be an image with an arbitrary pattern. If it is only a monotonous or repeated pattern, such as a stripe pattern or a grid pattern and no image with an arbitrary pattern can be formed, it cannot be considered as "imaging".

As used herein, the term "periocular region" refers to the region including the following facial regions and combinations thereof: the lower eye socket, the inner corner of an eye, the outer corner of an eye, the upper eyelid, the nasal bridge, the nasal root, the temporal region, the forehead, and the cheekbone.

As used herein, the expression "a projection of the light-emitting surface of the light source and a projection of the imaging plane on the same parallel plane have an overlapping region" means that the projection of the light-emitting surface on a plane parallel to the light-emitting surface has an overlapping region with the projection of the imaging plane on the same parallel plane.

As used herein, the term "included angle between the light-emitting surface and the imaging plane" refers to the dihedral angle formed when the light-emitting surface and the imaging plane are extended and intersect, and the angle is 0 degrees if the light-emitting surface is parallel to the imaging plane.

As used herein, the term "roughly parallel" means that the included angle between the "imaging plane" and the "light-emitting surface" is less than 30 degrees, preferably less than 10 degrees. When the light source is a flexible light source, the "light-emitting surface" may include a curved surface. However, it is to be noted that the light-emitting surface also includes a planar surface. The light-emitting surface of the planar surface is "roughly parallel" to the imaging plane, and the included angle is less than 30 degrees, preferably less than 10 degrees. At this point, the region of the "light-emitting surface" that is roughly parallel to the "imaging plane" accounts for at least 30%, preferably at least 50%, of the entire light-emitting surface.

Figure 6A:
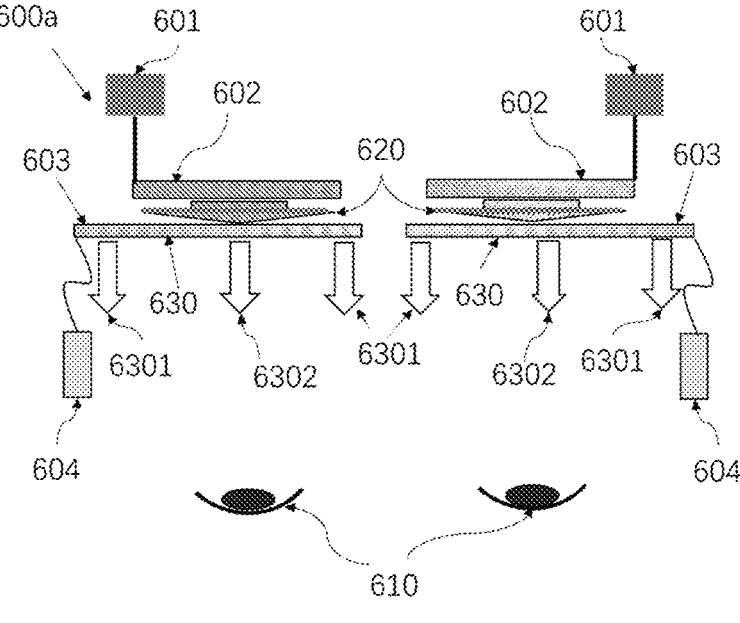
FIG. 6A is a schematic diagram of another wearable phototherapy display device.
Figure 6B:
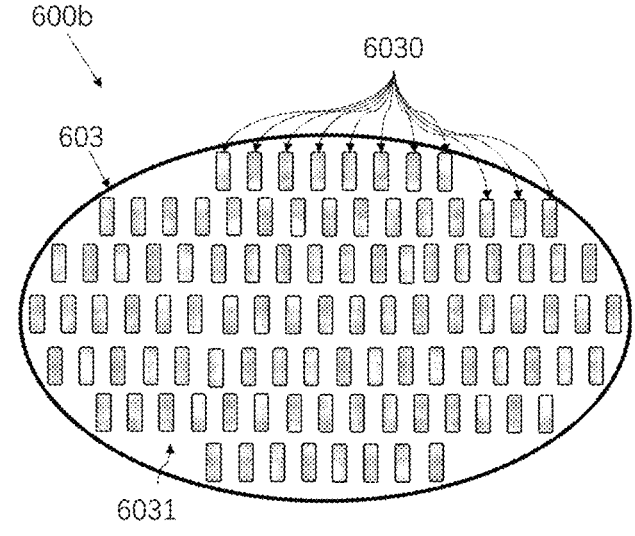
FIG. 6B is a schematic diagram of the preparation of a light source.

As used herein, the term "transmittance of the light source" refers to the ratio of the light intensity of the portion of the light emitted by any beam of incident light that can penetrate through the entire light source to the total light intensity of the incident light. If the light source itself is transparent (for example, an OLED light-emitting panel emitting light on both sides), the "transmittance of the light source" is the ratio of the light intensity of the portion of any beam of incident light that penetrates through the light-emitting region of the light source to the total light intensity of the incident light. If the light source is a series of non-transparent light sources arranged in an array, the "transmittance of the light source" is the ratio of the sum of areas of transparent regions to the total area of the light source region in the entire light source region. For example, as shown in FIG. 6B, the "transmittance of the light source" refers to the ratio of the sum of areas of the blank regions 6031 to the total area of the light sources 603.

As used herein, the term "front side of the imaging plane" refers to the side of the imaging plane adjacent to the human eye; and the term "back side of the imaging plane" refers to the side of the imaging plane away from the human eye. According to an embodiment of the present disclosure, disclosed is a wearable phototherapy display, which includes:

a display unit and a light source;

wherein the display unit has an imaging plane, and the imaging plane is disposed directly in front of the human eye;

the light source emits light having a peak wavelength between 400 nm and 1400 nm, and the light emitted by the light source is directed towards at least a part of a periocular region; and the light source includes a light-emitting surface, and an included angle between the light-emitting surface and the imaging plane is less than 30 degrees.

According to an embodiment of the present disclosure, the included angle between the light-emitting surface and the imaging plane is less than 10 degrees.

According to an embodiment of the present disclosure, the included angle between the light-emitting surface and the imaging plane is equal to 0 degrees.

According to an embodiment of the present disclosure, the light source emits light having a peak wavelength between 500 nm and 1400 nm.

According to an embodiment of the present disclosure, the light source emits light having a peak wavelength between 600 nm and 1000 nm.

According to an embodiment of the present disclosure, the light source emits light having a peak wavelength between 680 nm and 1000 nm.

According to an embodiment of the present disclosure, the light source includes an OLED light source, and the OLED light source includes at least one OLED light-emitting panel.

According to an embodiment of the present disclosure, the light source includes an OLED light source, and the OLED light source includes multiple OLED light-emitting panels.

According to an embodiment of the present disclosure, the OLED light source is flexible.

According to an embodiment of the present disclosure, the OLED light-emitting panel includes multiple OLED devices (OLED units), the multiple OLED devices (OLED units) are spaced apart from each other such that the transmittance of the light source is greater than or equal to 30%.

According to an embodiment of the present disclosure, the OLED light-emitting panel includes multiple OLED devices (OLED units), the multiple OLED devices (OLED units) are spaced apart from each other such that the transmittance of the light source is greater than or equal to 50%.

According to an embodiment of the present disclosure, the OLED light-emitting panel includes multiple OLED devices (OLED units), the multiple OLED devices (OLED units) are spaced apart from each other such that the transmittance of the light source is greater than or equal to 70%.

According to an embodiment of the present disclosure, the multiple OLED light-emitting panels are spaced apart from each other such that the transmittance of the light source is greater than or equal to 30%.

According to an embodiment of the present disclosure, the multiple OLED light-emitting panels are spaced apart from each other such that the transmittance of the light source is greater than or equal to 50%.

According to an embodiment of the present disclosure, the multiple OLED light-emitting panels are spaced apart from each other such that the transmittance of the light source is greater than or equal to 70%.

According to an embodiment of the present disclosure, the OLED light source includes a top-emitting device.

According to an embodiment of the present disclosure, the OLED light source includes a stacked device.

According to an embodiment of the present disclosure, the OLED light source includes a double-sided light-emitting device.

According to an embodiment of the present disclosure, the wearable phototherapy display device includes a drive device, and the drive device is electrically connected to the light source.

According to an embodiment of the present disclosure, the drive device includes any one or more of the following components: a power supply, a charging device, a Bluetooth communication device, a chip, a lead, a circuit board and a switch.

According to an embodiment of the present disclosure, the power supply includes a battery.

According to an embodiment of the present disclosure, the battery is selected from any one or more of a thin-film battery, a microbattery, a button battery, a chemical battery, a lithium battery or a hydrogen battery.

According to an embodiment of the present disclosure, the drive device is capable of being wirelessly connected to an external electronic device.

According to an embodiment of the present disclosure, the drive device includes a Bluetooth communication device and is capable of being wirelessly connected to the external electronic device through the Bluetooth communication device.

According to an embodiment of the present disclosure, the external electronic device further includes an application (APP), and the external electronic device is capable of controlling the light source on and off through the APP, and/or controlling the light source to adjust brightness of the light source through the APP.

According to an embodiment of the present disclosure, the drive device independently drives at least two OLED light-emitting panels.

According to an embodiment of the present disclosure, the drive device independently drives at least two OLED devices.

According to an embodiment of the present disclosure, the display unit is a micron display unit.

According to an embodiment of the present disclosure, the micron display unit uses any one or more of an OLED, a micro LED or a laser as a display light source.

According to an embodiment of the present disclosure, the wearable phototherapy display device includes an optical waveguide lens.

According to an embodiment of the present disclosure, a projection of the light-emitting surface of the light source and a projection of the imaging plane on the same parallel plane have an overlapping region.

According to an embodiment of the present disclosure, an overlapping region between the light-emitting surface of the light source and the imaging plane does not emit light.

According to an embodiment of the present disclosure, the periocular region includes the following regions and combinations thereof: the lower eye socket, the inner corner of an eye, the outer corner of an eye, the upper eyelid, the nasal bridge, the nasal root, the temporal region, the forehead, and the cheekbone.

According to an embodiment of the present disclosure, the light source is disposed on the front side of the imaging plane.

According to an embodiment of the present disclosure, the light source is disposed on the back side of the imaging plane.

According to an embodiment of the present disclosure, the light source is disposed on the side of the imaging plane away from the human eye.

According to an embodiment of the present disclosure, the light source is disposed on the side of the imaging plane close to the human eye.

According to an embodiment of the present disclosure, the display unit is electrically connected to the drive device.

According to an embodiment of the present disclosure, the wearable phototherapy display device is a pair of VR glasses.

According to an embodiment of the present disclosure, the wearable phototherapy display device is a pair of AR glasses.

According to an embodiment of the present disclosure, the wearable phototherapy display device is a helmet with a display.

The structure diagram of a typical single-layer OLED device 100 is shown in FIG. 1A. The OLED device 100 includes an anode layer 101, a hole injection layer (HIL) 102, a hole transport layer (HTL) 103, an electron blocking layer (EBL) 104, an emissive layer (EML) 105, a hole blocking layer (HBL) 106, an electron transport layer (ETL) 107, an electron injection layer (EIL) 108, a cathode layer 109, and a capping layer (CPL) 110. In a bottom-emitting device, the anode layer 101 is made of a transparent or translucent material, where the material includes, but is not limited to, indium tin oxide (ITO), indium zinc oxide (IZO), molybdenum oxide (MoOx) and the like, and the transparency of the material is generally greater than 50%, preferably greater than 70%. The cathode layer 109 is made of a material having high reflectivity, where the material includes, but is not limited to, Al, Ag and the like, and the reflectivity of the material is greater than 70%, preferably greater than 90%. In a top-emitting device, the anode layer 101 is made of a material with high reflectivity or a combination of materials with high reflectivity, where the material includes, but is not limited to, Ag, Ti, Cr, Pt, Ni, TiN, and combinations thereof with ITO and/or MoOx, and the reflectivity of the material is generally greater than 50%, preferably, greater than 80%, and more preferably, greater than 90%. The cathode layer 109 should be made of a translucent or transparent conductive material, where the material includes, but is not limited to, an Mg—Ag alloy, MoOx, Yb, Ca, ITO, IZO or a combination thereof, and the transparency of the material is generally greater than 30%, preferably, greater than 50%. In a double-sided light-emitting device, both the anode layer 101 and the cathode layer 109 are made of transparent or translucent materials as described above. The hole injection layer 102 may be a single material layer such as the commonly used HATCN. The hole injection layer 102 may also be made of a hole transport material doped with a certain proportion of a p-type conductive doping material, where the doping proportion is generally not higher than 5% and is commonly between 1% and 3%. The emissive layer 105 generally further includes at least one host material and at least one emissive material, the electron blocking layer 104 and the hole blocking layer 106 are optional layers, and the capping layer 110 may not be required in the bottom-emitting device. The electron injection layer 107 may be a single layer of Yb, LiQ or LiF or may be formed with two or more materials via co-deposition.

Figure 1B:
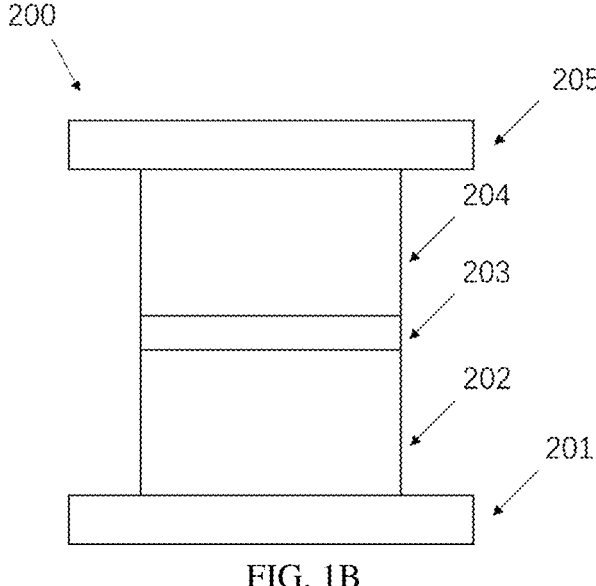
FIG. 1B is a structure diagram of a stacked OLED device.
Figure 2A:
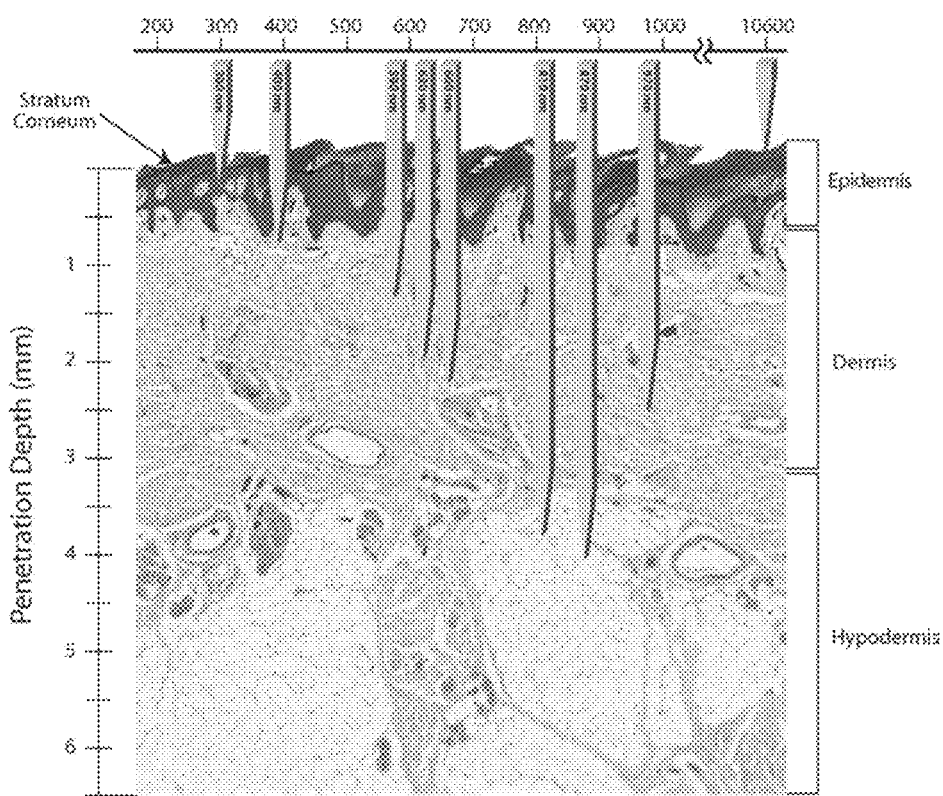
FIG. 2A is a schematic diagram of the penetration depth of light of different wavelengths into the skin tissue.
Figure 2B:
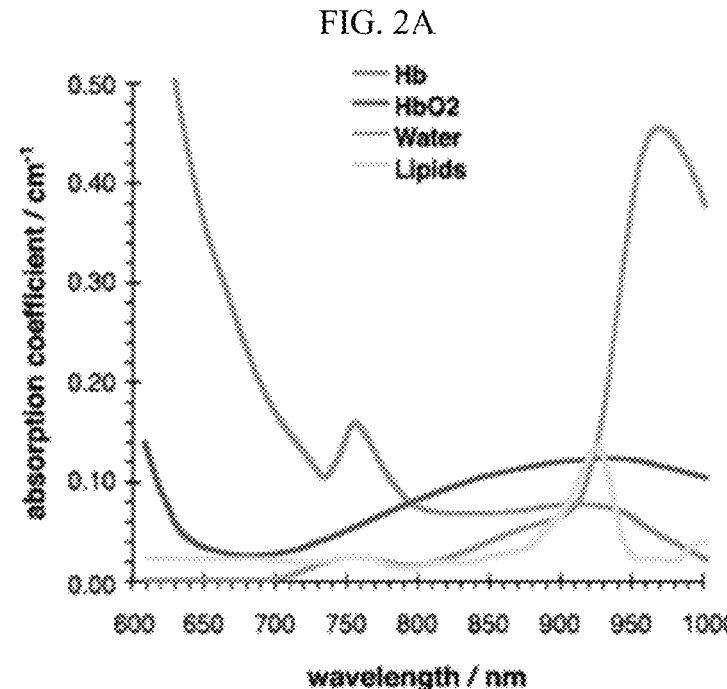
FIG. 2B is a schematic diagram of the absorption of light of different wavelengths of different physiological sub-stances (such as water, hemoglobin, oxyhemoglobin, and melanin).
Figure 2C:
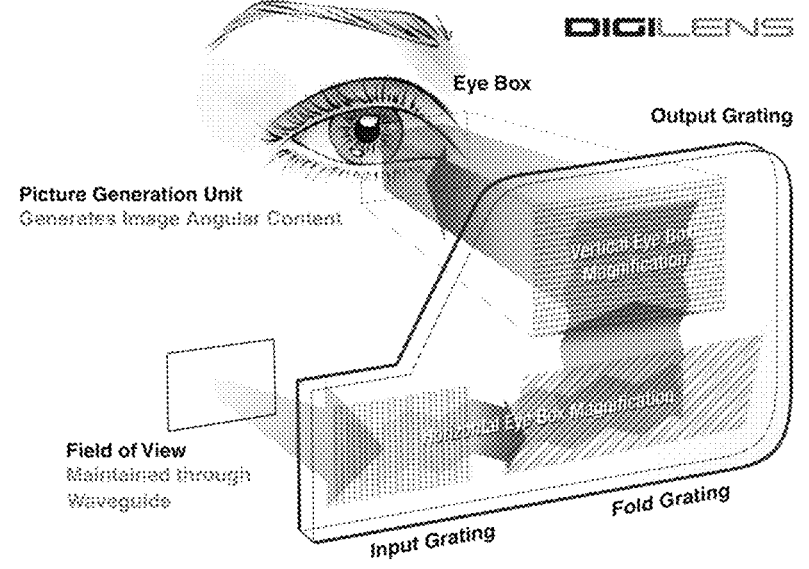
FIG. 2C is a principle diagram of the transfer of images in front of the human eye through an optical waveguide lens in the related art.

The structure diagram of a typical stacked OLED device 200 is shown in FIG. 1B. The stacked OLED device 200 includes an anode layer 201, a first light-emitting sub-unit 202, a charge generation layer (CGL) 203, a second light-emitting sub-unit 204, and a cathode layer 205. The first light-emitting sub-unit 202 and the second light-emitting sub-unit 204 may further include a series of organic layers including layers from the hole injection layer 102 to the electron injection layer 108 in the single-layer light-emitting device 100, and the emissive layers of the first light-emitting sub-unit 202 and the second light-emitting sub-unit 204 may be the same or different. The first light-emitting sub-unit 202 and the second light-emitting sub-unit 204 may emit light of the same color. For example, the first light-emitting sub-unit 202 and the second light-emitting sub-unit 204 both emit red light having a peak wavelength between 600 nm and 750 nm. The first light-emitting sub-unit 202 and the second light-emitting sub-unit 204 may also emit light of different colors. For example, the first light-emitting sub-unit 202 emits red light and the second light-emitting sub-unit 204 emits near-infrared light having a peak wavelength between 750 nm and 1400 nm. At this point, the device 200 may emit red light and near-infrared light simultaneously. The charge generation layer 203 is generally composed of an n-type material and a p-type material, and a buffer layer may be added as described in patent application CN112687811A. If the stacked device is a top-emitting device, a capping layer may also be added on the cathode layer 205. FIG. 1B shows a two-unit stacked device, and on the basis of the device shown in FIG. 1B, a third light-emitting sub-unit and a second charge generation layer may be added to form a three-unit stacked device. The preparation of single-layer and stacked OLED devices is well known in the industry, and the details will not be repeated here.

Figure 3A:
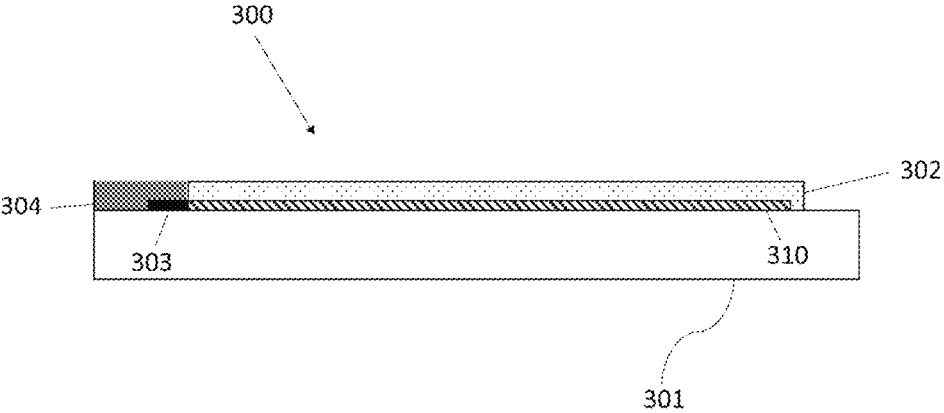
FIGS. 3A to 3D are cross-sectional views of an OLED light-emitting panel.
Figure 3B:
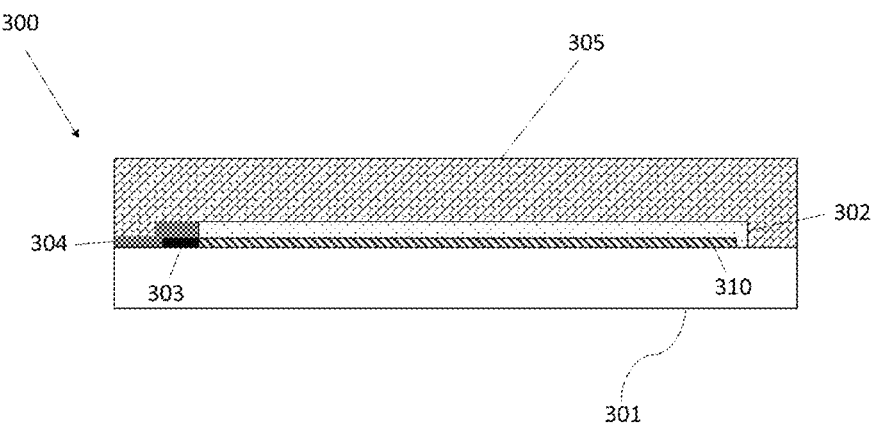
Figure 3C:
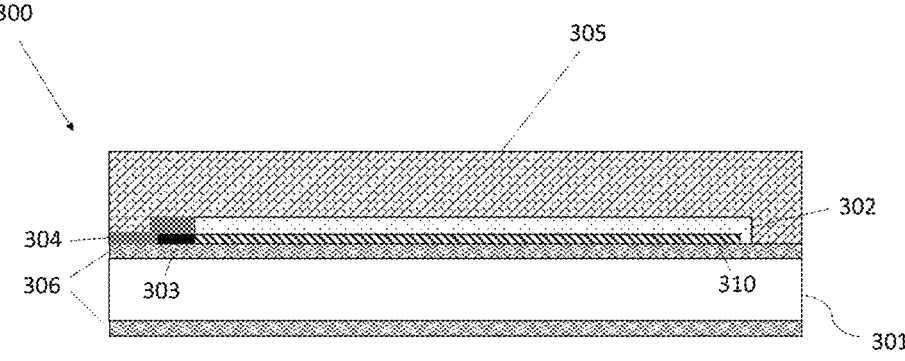
Figure 3D:
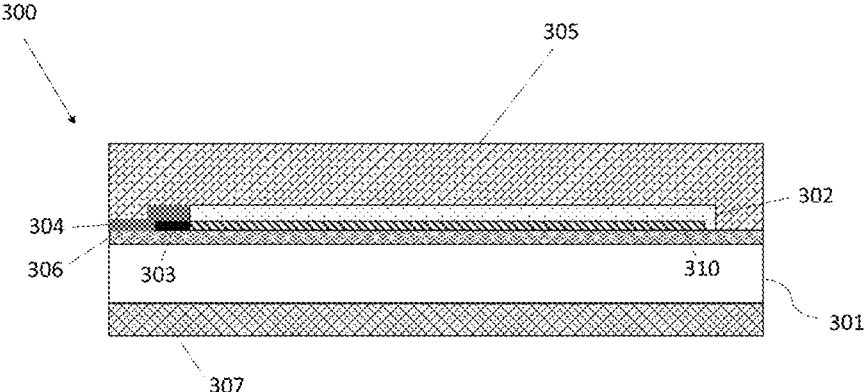

One light source that can be used in the wearable phototherapy display device is an organic electroluminescent device (OLED). The cross-sectional views of OLED light-emitting plane are shown in FIGS. 3A to 3D. In FIG. 3A, the OLED light-emitting panel 300 includes a substrate 301, one OLED device 310, a pair of contact electrodes 303 electrically connected to the OLED device 310, an encapsulation layer 302 (with the contact electrodes 303 exposed), and an adhesive structure 304 connecting the pair of contact electrodes 303 to an external drive circuit. The substrate 301 may be hard, such as glass, quartz plates and the like. The substrate 301 is preferably flexible, including, but not limited to ultra-thin flexible glass, polyethylene terephthalate (PET), polyethylene naphthalate (PEN), polyimide (PI) and the like. In particular, the substrate 301 may be prepared by curing and planarizing a material (for example, a PI material) previously coated on a support baseplate in a solution form and then used for device preparation. After the device preparation is completed, the material is peeled off from the support baseplate by laser and transferred to other flexible substrates as required. The OLED device 310 may be a bottom-emitting device or a top-emitting device. Preferably, the OLED device 310 is a top-emitting device because the light-emitting efficiency of the top-emitting device is higher. The OLED device 310 may be in a single-layer structure or may be in a stacked structure. Preferably, the OLED device 310 has a stacked structure because the stacked structure enables the device to have a longer lifetime at the same brightness and the thicker film layer of the stacked structure can improve the production yield. The organic materials in the OLED device 310 may be deposited by thermal evaporation in a vacuum chamber, or may be partially or completely formed by a solution process including but not limited to inkjet printing, spin coating, organic vapor jet printing (OVJP) and the like. The encapsulation layer 302 may be a hard encapsulation. For example, the encapsulation is achieved by bonding a cover glass to the substrate with a UV-cured encapsulation adhesive. Preferably, the encapsulation layer 302 is a thin-film encapsulation layer usually with a thickness of 10 μm and above. For example, the thin-film encapsulation layer is a single inorganic layer or a thin-film multi-layer structure in which organic and inorganic layers alternate, where the film is formed by plasma-enhanced chemical vapor deposition (PECVD), atomic layer deposition (ALD), printing, spin coating and the like. The encapsulation layer 302 may also use a combination of the above two types of encapsulation layers, that is, a cover glass encapsulation is performed on the basis of the thin-film encapsulation. The contact electrodes 303 may include at least one anode contact and at least one cathode contact. A front cover film 305 may be added on the above-mentioned OLED light-emitting panel, as shown in FIG. 3B. The front cover film 305 may be a flexible printed circuit (FPC) board on which a pre-designed circuit is printed, and is electrically connected to the OLED device 310 through the adhesive structure 304. In another solution, the adhesive structure 304 may be an FPC frame, and the front cover film 305 may be a plastic thin film to provide mechanical support. The specific description of the use of an FPC board to drive an OLED light-emitting panel can be found in patent application US20190376650A1, which is incorporated by reference in its entirety and is not within the scope of the detailed description of the present application. The front cover film 305 may also include a light extraction layer. When the OLED device 310 is a top-emitting device, the front cover film 305 is transparent in the light-emitting region. The front cover film 305 may be a combination of various forms of films described above. An additional thin-film encapsulation layer 306 may be coated on one or two sides of the substrate 301, as shown in FIG. 3C. The front cover film may also be coated with an additional thin-film encapsulation layer 306. In FIG. 3D, the back cover film 307 is covered on the substrate 301. The back cover film 307 may be used for mechanical support and is also usually a flexible thin film, for example, a plastic such as PET. When the OLED device 310 is a bottom-emitting device, the back cover film 307 may be a light extraction layer and is transparent. The back cover film 307 may be a combination of various forms of films described above. When one or more OLED light-emitting panels are electrically connected to an external electric drive (whether in an on or off state), one OLED light source is formed, which is one of the basic constituent elements of the present disclosure.

Figure 4A:
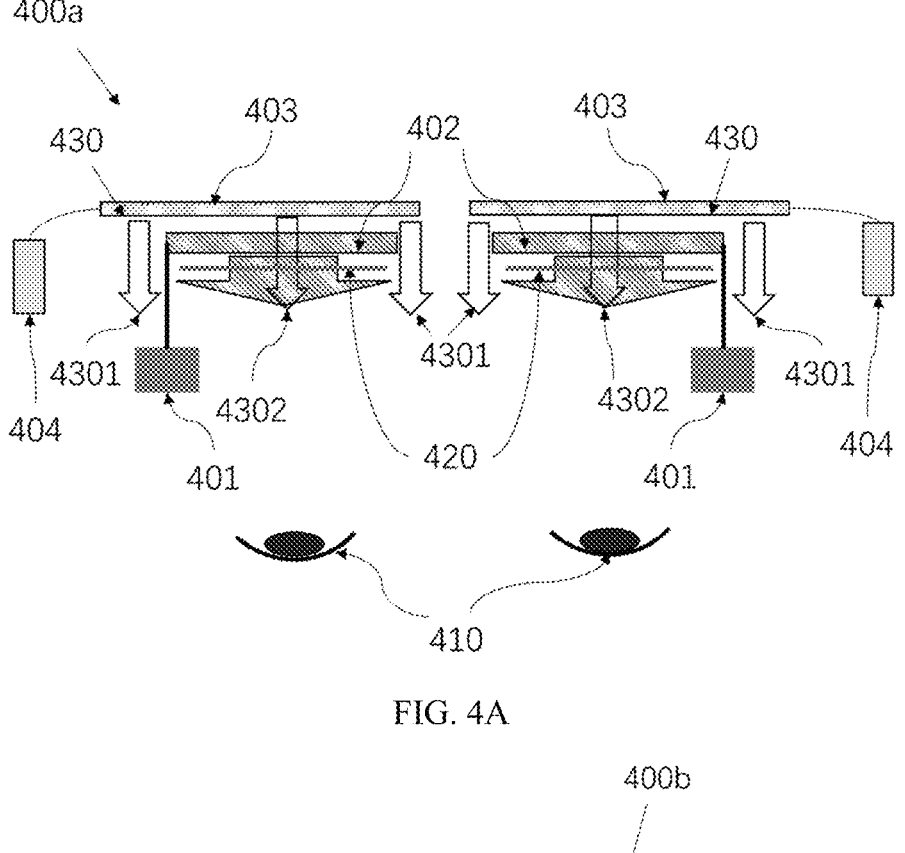
FIG. 4A is a schematic diagram of a wearable photo-therapy display device.

FIG. 4A shows a schematic diagram of a wearable phototherapy display device 400a. The wearable phototherapy display device 400a includes light sources 403, drive devices 404, micron display units 401, and optical waveguide lenses 402. The two light sources 403 are each electrically connected to one drive device 404. The two optical waveguide lenses 402 are each connected to a respective one of two micron display units 401 disposed on two sides of the human face through optical paths respectively, that is, the imaging can be formed in front of the human eye 410. At this point, each imaging plane 420 is between an optical waveguide lens 402 and the human eye 410, as shown in FIG. 4A. Each imaging plane 420 is roughly parallel to the light-emitting surface 430 of a respective one of the two light sources 403. It is to be noted that the position of the imaging plane 420 shown in FIG. 4A is only an example, and the imaging plane 420 may be any plane between the human eye 410 and the optical waveguide lens 402. It is to be noted that the area of the optical waveguide lens 402 may be larger than the area of the imaging plane 420, that is, only a portion of the optical waveguide lens 402 may be the imaging region, and the remaining portion of the lenses may only be used for transferring the image but cannot form imaging on the imaging plane. The light source 403 is preferably an OLED light source and may be an OLED light-emitting panel disposed roughly parallel behind each of the two optical waveguide lenses 402, instead of being disposed around each of the two optical waveguide lenses 402. That is, each light source 403 is disposed on the back side of a respective one of the two imaging planes 420, the side away from the human eye 410, that is, each light source 403 is not disposed around a respective one of the two imaging planes 420. Each light source 403 has a light-emitting surface 430 which is the surface of the OLED light-emitting panel on the side close to the human eye. Each light-emitting surface 430 is roughly parallel to a respective one of the two imaging planes 420, that is, the included angle between the "imaging plane" and the "light-emitting surface" is less than 30 degrees, preferably less than 10 degrees, and more preferably equal to 0 degrees. FIG. 4A shows schematically that the light source 403 is disposed completely parallel behind each of the two optical waveguide lenses 402, that is, the included angle between the "imaging plane" and the "light-emitting plane" is equal to 0 degrees. Each light-emitting surface 430 can be divided into a region 4301 and a region 4302. The light emitted from the region 4301 is directed towards the skin of a part of the periocular region, such as the lower eye socket, the inner corner of an eye, the outer corner of an eye, the upper eyelid, the nasal bridge, the nasal root, the temporal region, the forehead, and the cheekbone, and the region 4301 does not overlap with the imaging plane 420. Most of the light emitted from the region 4301 is directed towards the periocular region, but not towards the human eye. Meanwhile, the light emitted from the region 4302 is directed towards the imaging plane 420, passes through the imaging plane 420 and is mainly emitted towards the human eye. At this point, the projection of the light-emitting surface 430 and the projection of the imaging plane 420 on the same parallel plane have an overlapping region. That is, it indicates that the light source 403 is disposed roughly parallel on the back side of each of the two optical waveguide lenses 402, instead of being disposed around each of the two optical waveguide lenses 402, that is, the light source 403 is not disposed around each of the two imaging planes 420. The light source 403 emits light having a peak wavelength between 400 nm and 1400 nm, and the light source 403 is not a display unit and cannot form imaging. The micron display unit 401 can form imaging by using a white light source and filters on a silicon wafer to form red, green, and blue pixels, and the white light source is preferably an OLED light source. The micron display unit 401 can also form imaging by preparing red, green and blue pixels that are side-by-side arranged on a silicon wafer using an OLED, and the advantage of this manner is that it can achieve higher brightness. The micron display unit 401 can also form imaging by transferring and integrating blue light micro LEDs onto silicon wafers, red green blue pixels are achieved through down-conversion and filters, or by directly transferring and integrating red, green, and blue micro LEDs onto silicon wafers. The micron display unit 401 may also be a laser display which has higher brightness and is particularly suitable for producing AR products. The optical waveguide lens may be a transparent lens, on the surface of which a series of micro patterns with specific sizes are set, and can transmit images from one end to the other by the double reflection of light. The preparation and principle of micron display units and optical waveguide lenses can be found in various publications, patents and websites (arvrjourney.com), which is well known to those skilled in the art, and the details will not be repeated here. The light source 403 emits light having a peak wavelength between 400 nm and 1400 nm, preferably, light having a peak wavelength between 500 nm and 1000 nm, more preferably, light having a peak wavelength between 600 nm and 1000 nm, and still more preferably, light having a peak wavelength between 680 nm and 1000 nm. Green light having a wavelength between 500 nm and 600 nm can stimulate the eyeball and ameliorate retinal diseases and maculopathy caused by diabetes. The light having a wavelength between 600 nm and 1000 nm has an effective wavelength band of red light therapy and can be used to remove wrinkles, remove spots, and moisturize the skin. Finally, since the human eye is very insensitive to light having a wavelength between 680 nm and 1000 nm, such light can hardly disturb normal display and normal vision. Although the light having a wavelength between 400 nm to 680 nm can be observed by human eyes, when people view some static, black-and-white, or text-type images, the colors around the images or colors of these images do not affect the viewing experience too much. Further, in some practical applications, users can turn off images after viewing a segment of images and turn on the OLED light source emitting light having a wavelength between 500 nm and 600 nm to relieve eyeballs, or diabetic patients can use the light of such wavelengths to treat retinal diseases or maculopathy. Meanwhile, since the light source 403 is disposed behind each of the two optical waveguide lenses 402 and each optical waveguide lens 402 is translucent or even transparent, the light emitted by the light source 403 can almost 100% penetrate through the optical waveguide lens and reach the human eye and the periocular region. Therefore, such a wearable phototherapy display device can simultaneously achieve the functions of display and phototherapy. Each drive device 404 is electrically connected to a respective one of the two light sources 403 (shown in FIG. 4A), and the electrical connection includes, but is not limited to, one or more of thin-film metal, transparent conductive materials or FPC leads. The drive device 404 includes, but is not limited to, one or more of a power supply, a charging device (preferably a wireless charging device), a Bluetooth communication device, a chip, a lead, a circuit board or a switch, where the power supply includes a battery, and the battery may be selected from one or more of a thin-film battery, a microbattery, a button battery, a chemical battery, a lithium battery or a hydrogen battery. The drive device 404 may also be wirelessly connected to an external electronic device through the Bluetooth communication device and controlled by the external electronic device to achieve, for example, switching on or off, brightness adjustment and region-based control. The external electronic device may be a smart phone, a smart watch, a tablet, a notebook computer, a computer and other devices. Further, the external electronic device may be combined with an application (APP) for control. The drive device 404 may also be integrated into the micron display unit 401, and then the drive device 404 and the micron display unit 401 are controlled by the external electronic device.

Figure 4B:
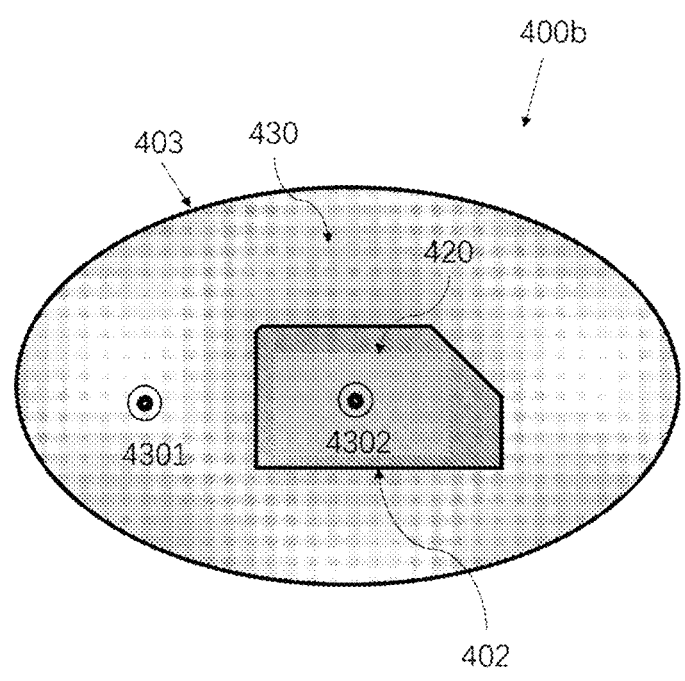
FIG. 4B is a schematic diagram of the relative area and positional relationship of projections of the light-emitting surface and the imaging plane in FIG. 4A on the same parallel plane.

FIG. 4B shows a schematic diagram 400b of the relative area and positional relationship of projections of the light-emitting surface 430 of the light source 403 and the imaging plane 420 in FIG. 4A on the same parallel plane. The light source 403 is disposed roughly parallel on the side of the optical waveguide lens 402 away from the human eye, that is, the light-emitting surface 430 of the light source 403 is roughly parallel to the imaging plane 420. The light-emitting surface 430 of the light source 403 produces the region 4301 and the region 4302 for phototherapy, and the optical waveguide lens 402 produces the imaging plane 420 for display. The projection of the light-emitting surface 430 of the light source 403 and the projection of the imaging plane 420 on the same parallel plane has a partially overlapping region, and the projection of the light-emitting surface 430 on the same parallel plane completely covers the projection of the imaging plane 420 on the same parallel plane, where the region of the imaging plane 420 completely overlaps with the region 4302 and does not overlap with the region 4301. It is to be noted that since the area of the optical waveguide lens 402 may be slightly greater than the area of the human eye region and the area of the imaging plane 420 may be less than the area of the optical waveguide lens 402, the projections of the light-emitting surface 430 and the optical waveguide lens 402 on the same parallel plane may have a partially overlapping region, such as the region shown by oblique lines in FIG. 4B. Assuming that the light emitted from the light source 403 is emitted outside the paper ("⊙" represents emitting outside the paper), the image projected by the optical waveguide lens 402 is also emitted outside the paper and forms the imaging plane 420. The light source 403 may be hard or flexible. Preferably, the light source 403 is flexible so that the weight and volume can be reduced and the light source 403 can cling to the optical waveguide lens 402 to further compress space. When the light source 403 is a flexible light source, the light source 403 may be further bent and covers facial regions such as temples and cheeks. At this point, the light-emitting surface 430 may also include a curved surface. However, it is to be noted that the portion where the light-emitting surface 430 covers the human eye and the periocular region (for example, the eye socket, the outer corner of an eye, and the eyebrow) is still planar. Therefore, the light-emitting surface 430 is still roughly parallel to the imaging plane or the included angle with the light-emitting surface 430 and the imaging plane is less than 30 degrees.

Figure 4C:
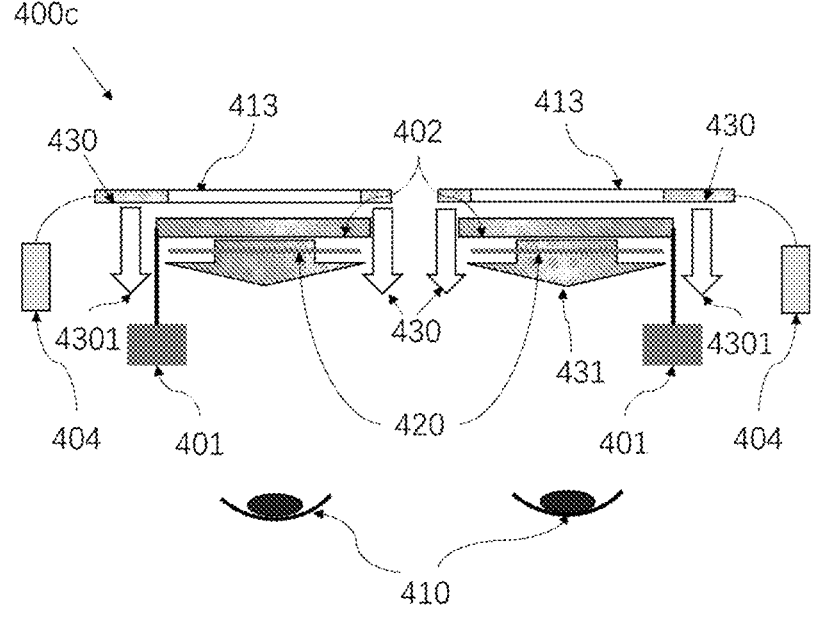
FIG. 4C is another schematic diagram of a wearable phototherapy display device.
Figure 4D:
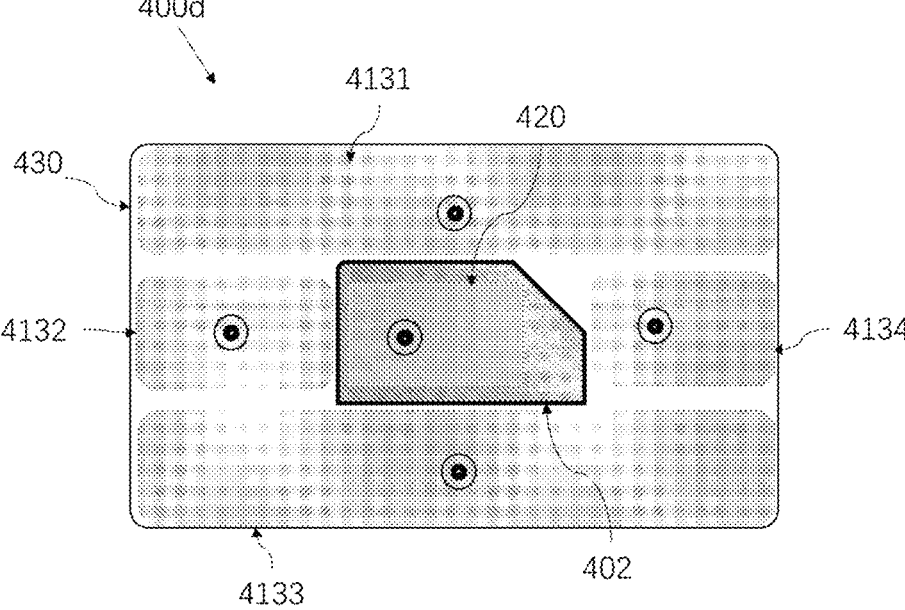
FIG. 4D to 4E are schematic diagrams of the relative area and positional relationship of projections of the light-emit-ting surface and the imaging plane in FIG. 4C on the same parallel plane.
Figure 4E:
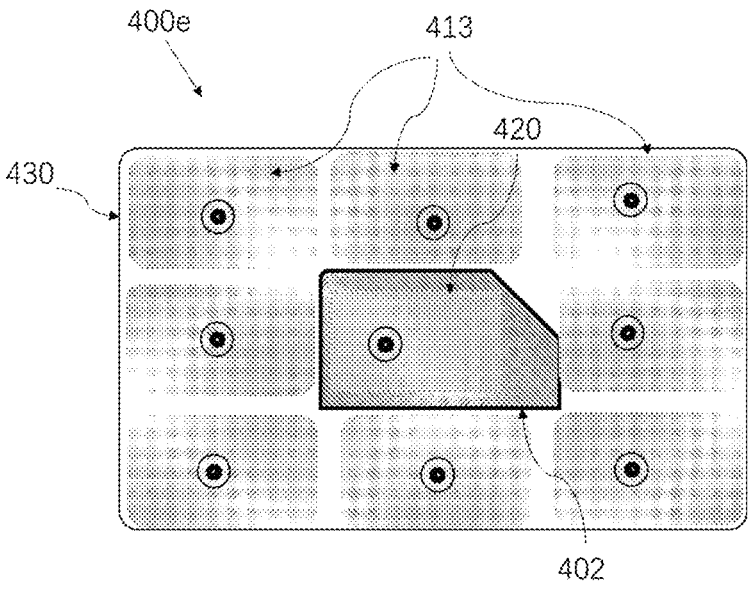

In FIG. 4B, all regions of the light source 403 emit light and the projections of the light-emitting surface 430 of the light source 403 and the imaging plane 420 on the same parallel plane have an overlapping region (region 4302). However, considering that in most of the time, people wear such a wearable phototherapy display device to view images, if only the skin of the periocular region is treated, no light needs to be emitted to the eyeball. Therefore, the region (for example, the region 4302 in FIGS. 4A and 4B) where the light-emitting surface overlaps with the imaging plane may be made not to emit light or is provided with no OLED light-emitting panel, that is, only the region 4301 emits light. It is to be noted that most of the light emitted from the region 4301 at this point is directed towards the skin of the periocular region, but not directly towards the human eye. In the schematic diagram of the wearable phototherapy display device as shown in FIG. 4C, the block processing may be performed on each light source 413. Each light source 413 may be divided into multiple light-emitting sub-regions, and at this point, the light source 413 is still preferably an OLED light source. FIG. 4D shows a schematic diagram of the relative area and positional relationship of projections of the light-emitting surface 430 of the light source 413 and the imaging plane 420 in FIG. 4C on the same parallel plane. At this point, the light source 413 is divided into multiple light-emitting sub-panels 4131, 4132, 4133, and 4134. Each light-emitting sub-panel is electrically connected to a respective one of the drive devices 404, and preferably, each light-emitting sub-panel may be independently driven by the drive device 404. It is to be noted that since the area of the optical waveguide lens 402 may be slightly greater than the area of the human eye region and the area of the imaging plane 420 may be less than the area of the optical waveguide lens 402, the projections of the light-emitting surface 430 of an OLED light-emitting sub-panel and the optical waveguide lens 402 on the same parallel plane may have a partially overlapping region, such as the region shown by oblique lines in FIG. 4D. However, at this point, the light-emitting surface 430 does not overlap with the imaging plane 420. At this point, although the light-emitting surface 430 of the light source 413 is mainly at the periphery of the imaging plane 420, the OLED light source is still roughly parallel on one side of the optical waveguide lens 402, that is, the light-emitting surface 430 of the OLED light source is still roughly parallel to the imaging plane 420. Similarly, the OLED light-emitting sub-panels 4132 and 4134 in FIG. 4D are preferably flexible and may also be bent to wrap and fit the temple regions on two side of the human face to further expand the treatment region. It is to be noted that the light-emitting region of the OLED light-emitting panel may also include the forehead portion. Preferably, the light source 413 may also be a series of OLED light-emitting panels of the same layout to reduce production costs, as shown in FIG. 4E. The advantage of integrating a series of flexible OLED light-emitting panels as shown in FIGS. 4D to 4E is that each panel can be driven independently, or that the panels can be grouped according to corresponding human eye parts, panels in one group can be driven simultaneously, and panels in different groups can be driven independently. For example, panels corresponding to the outer corner of an eye and the lower eye socket are grouped into one group, panels corresponding to the upper eye socket and the forehead are grouped into one group, and each group of panels may be driven independently. The resulting optional local light can further reduce the power consumption and save energy. Meanwhile, different emission wavelengths can be selected according to the different needs of phototherapy regions. For example, the light of the wavelength of 600 nm is emitted to whiten the skin, because the wavelength of this band has the most significant effect on melanin and can ameliorate dark eye circles. The light of the wavelength of 700 nm is emitted to moisturize and rejuvenate the skin, because the light of this band can be absorbed by water in the human body and can achieve the effect of wrinkle removal and skin firming. The light of the wavelength of 530 nm is emitted to treat maculopathy. Such a wearable phototherapy display device can not only provide display images, but also achieve the effects of skin whitening, skin rejuvenation, and eye disease treatment, achieving multiple purposes simultaneously. It is to be noted that although the light source in the present disclosure may display the light-emitting region and non-light-emitting region or the color of one region may be different from the color of another region, such a combination cannot achieve one specific image, and "imaging" still cannot be achieved. Such region-based control is achieved in the following methods.

Figure 5A:
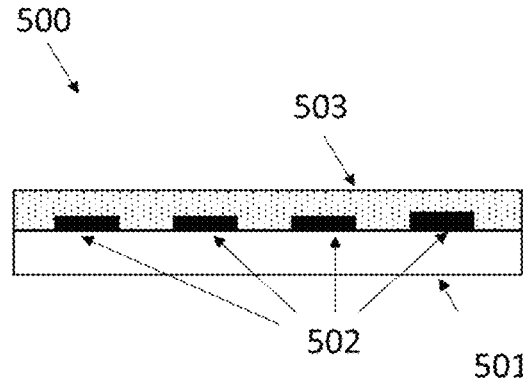
FIGS. 5A to 5C are schematic diagrams of an OLED light-emitting panel.

In one method, the pixelated layout is designed on the same large-area flexible OLED light-emitting panel, and then each pixel is driven independently or pixels are grouped and then driven independently in groups. The OLED light-emitting panel is flexible, that is, the light-emitting panel use flexible substrate and thin film encapsulation. The pixel here generally has a light-emitting area on the order of millimeters, that is, the minimum size of the pixel is greater than 1 mm², preferably greater than 5 mm². For example, a flexible OLED light-emitting panel 500 shown in FIG. 5A may include one flexible OLED substrate 501, a series of OLED devices 502 are fabricated by patterning on the flexible OLED substrate 501, and all of the devices share the same thin-film encapsulation layer 503. At this point, each light-emitting unit is one OLED device, and the whole flexible OLED light-emitting panel is one light source. Therefore, metal wiring may be arranged on the panel at the same time when the anode or cathode is prepared to electrically connect the respective OLED devices 502. The method of metal wiring is well known to those skilled in the art, and the details will not be repeated here. Different OLED devices are controlled through a circuit control system so that different devices can emit light of different colors or the same device works at different currents to emit multiple colors.

Figure 5B:
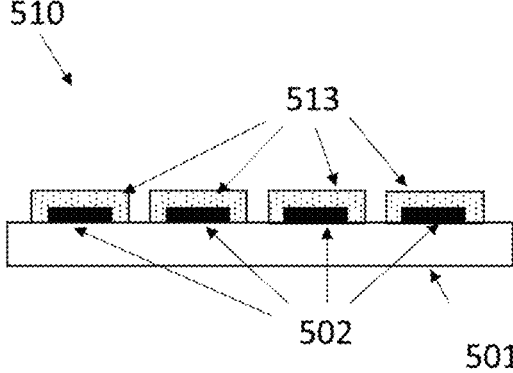

One deformation of the preceding solution is a flexible OLED light-emitting panel 510 shown in FIG. 5B. The flexible OLED light-emitting panel 510 includes one flexible OLED substrate 501 and a series of OLED devices 502. But each device has a separate encapsulation layer 513, and preferably, the encapsulation layer is a thin-film encapsulation layer. At this point, different OLED devices 502 can be connected not only through metal wiring, but also through an FPC circuit board, greatly increasing conductivity and circuit complexity. Similarly, a single OLED device 502 or multiple OLED devices 502 may be independently driven through these electrical connections. In the preceding two cases, if the light of different colors is to be emitted, different device structures may be evaporated for different OLED devices through metal masks, especially by changing the materials of emissive layers. As described in patent applications CN111081892A and CN111081891A, all devices use the same structure with an independent unit multi-emissive layer, and the color can be changed by moving the recombination region at different working points.

Figure 5C:
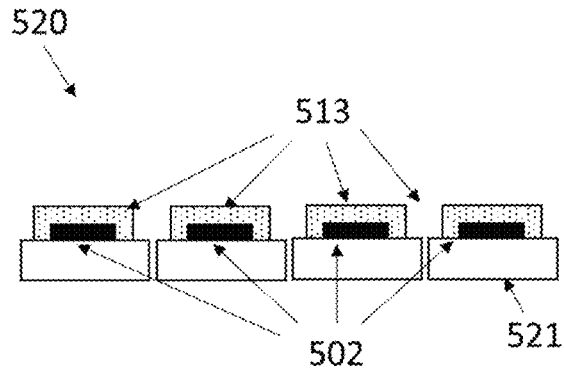

In another solution, independent OLED light-emitting panels are arranged into an array, as shown in FIG. 5C, and at this point, each OLED light-emitting panel includes one independent substrate 521, one OLED device 502, and one independent encapsulation layer 513. The advantage of the preceding arrangement is that even if non-flexible OLED light-emitting panels and/or non-flexible encapsulation layers are adopted, the light source formed into an array can still have certain flexibility as long as the area of each OLED light-emitting panel is small enough. But preferably, each independent OLED light-emitting panel may be flexible. These independent OLED light-emitting panels may be cut from the same motherboard. For example, the OLED light-emitting panels all use the same structure of an independent unit with multiple emissive layers. Alternatively, devices with different structures may be selected from different motherboards and then assembled. The advantage of the preceding solution is that the device can be screened, thereby improving the yield and increasing the diversity of product colors. The independent light-emitting panels shown in FIG. 5C may be arranged and combined by FPCs or front and back cover films according to requirements to form one array in which they are physically connected to each other. For details, reference may be made to the method disclosed in CN208750423U, and since it is not the focus of the present disclosure, the details will not be repeated here. Similarly, these panels can be independently controlled to be given different working currents. The preceding method can be used to prepare the combination form of multiple OLED light-emitting panels, as shown in FIGS. 4D to 4E.

Since some wearable phototherapy display devices are used for AR glasses, the light source 403 or 413 in FIGS. 4D to 4E needs to be transparent or translucent, and at this point, the light source is preferably an OLED light source. Therefore, the light source 403 or 413 may be disposed behind each of the optical waveguide lenses 402, as shown in FIGS. 4A to 4E. In the wearable phototherapy display device 600*a* shown in FIG. 6A, the light source 603 may also be disposed roughly parallel in front of each of the optical waveguide lenses 602, instead of being disposed around each of the optical waveguide lenses 602. That is, the light source 603 is disposed on the front side of each of the imaging planes 620, the side close to the human eye 610, that is, the light source 603 is not disposed around each of the imaging planes 620. At this point, the micron display units 601 may still be disposed on two sides of the human eye and are each optically connected to a respective one of the optical waveguide lenses 602 to form an imaging plane 620 in front of the human eye, and the imaging plane 620 is between the optical waveguide lens 602 and the human eye 610, as shown in FIG. 6A. As shown in FIG. 6A, each OLED light source 603 has a light-emitting surface 630, and at this point, the imaging plane 620 is roughly parallel to the light-emitting surface 630 of a respective one of the OLED light sources 603. Each light-emitting surface 630 is divided into regions 6301 and 6302. The region 6301 does not overlap with the imaging plane 620, and light emitted from the region 6301 is emitted towards the skin of the peripheral region of the human eye. The region 6302 overlaps with the imaging plane, and the light emitted from the region 6302 is directed towards the human eye. At this point, the projection of the light-emitting surface 630 and the projection of the imaging plane 620 on the same parallel plane have an overlapping region. That is, it indicates that the light source 603 is disposed roughly parallel on the front side of each of the optical waveguide lenses 602, instead of being disposed around each of the optical waveguide lenses 602, that is, the light source 603 is not disposed around each of the imaging planes 620. Transparent or translucent light sources may be prepared in various manners. For example, the light sources 603 may be two OLED light-emitting panels, and the OLED devices thereon may adopt a double-sided light-emitting structure, that is, both the anode layer and the cathode layer of the devices are made of transparent or semitransparent materials. For example, the anode layer is made of ITO, and the cathode layer is made of an Mg—Ag alloy. In this manner, the entire light source 603 appears to be transparent or translucent, and people can see the real world outside the lens while viewing images on the imaging plane 620 and can also receive phototherapy of the light-emitting region 6301 and the light-emitting region 6302 at the periocular region and on the eyes. When such a transparent light source 603 is disposed in front of each of the imaging planes 620 as in FIG. 6A, normal viewing of the display image will not be affected. For another manner to prepare the transparent light source, reference may be made to the previous application CN111538171A of the inventor, in which a series of (bottom-emitting or top-emitting) OLED devices or panels that are not double-sided light-emitting may be arranged in the form of an array to generate a certain transmittance. Specifically, as shown in the schematic diagram 600*b* in FIG. 6B, the light source 603 is composed of a series of OLED light-emitting panels or OLED device units 6030, and preferably, the light source 603 is composed of a series of OLED device units 6030. In this manner, with a smaller unit light-emitting area (opaque) and a denser arrangement manner, more blank regions 6031 are left for light transmission, and sufficient OLED device units 6030 are disposed to emit light to carry out phototherapy. The transmittance of the OLED light source composed of an OLED array or double-sided light-emitting devices is greater than or equal to 30%, preferably greater than or equal to 50%, and more preferably greater than or equal to 70%. It is to be noted that although the light source 603 is composed of a series of OLED devices, the light source 603 cannot form specific patterns, so "imaging" still cannot be achieved.

Figure 7A:
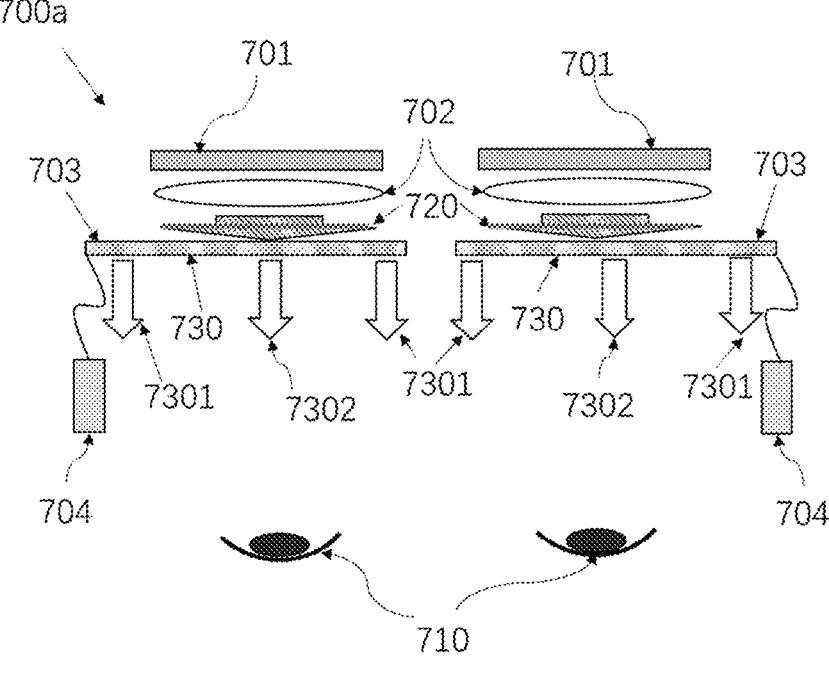
FIG. 7A is a schematic diagram of another wearable phototherapy display device.
Figure 7B:
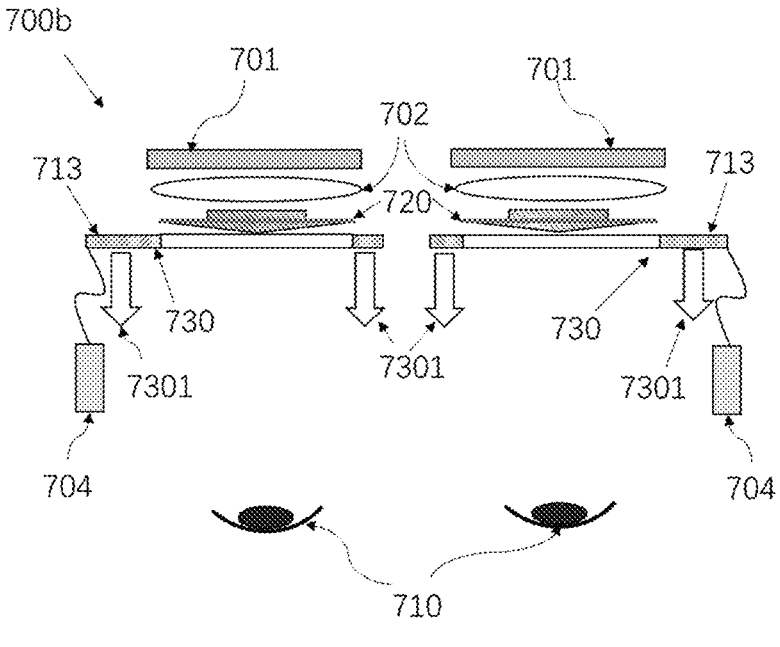
FIG. 7B is a schematic diagram of another wearable phototherapy display device.

The schematic diagram of another wearable phototherapy display device 700*a* is shown in FIG. 7A. A pair of silicon-based micron display units 701 is disposed directly in front of the human eyes 710. Since the micron display unit 701 is generally an opaque silicon-based display, the light source 703 may be disposed roughly parallel between a respective one of the micron display units 701 and the human eye. At this point, the imaging plane may be the display screen plane of each of the micron display units 701, and the light-emitting surface 730 of each light source 703 may be roughly parallel to a respective one of the imaging planes. If some optical lenses 702 are also (optionally) disposed directly in front of the micron display units 701 in the wearable phototherapy display device 700*a*, that is, an optical lens 702 is disposed between each micron display unit 701 and the human eye 710, the imaging plane 720 is also between each optical lens 702 and the human eye 710 and is roughly parallel to the light-emitting surface 730 of a respective one of the light sources 703, as shown in FIG. 7A. At this point, the light source 703 may be a transparent panel made of double-sided light-emitting devices or may be a transparent panel formed using the array shown in FIG. 6B. Of course, the structure of the wearable phototherapy display device 700*b* shown in FIG. 7B may also be adopted. The region where the light source 713 overlaps with the imaging plane 720 does not emit light or is provided with no OLED light-emitting panel. The description of FIG. 7B is similar to the above description of FIGS. 4C to 4E, and the details will not be repeated here.

Figure 8A:
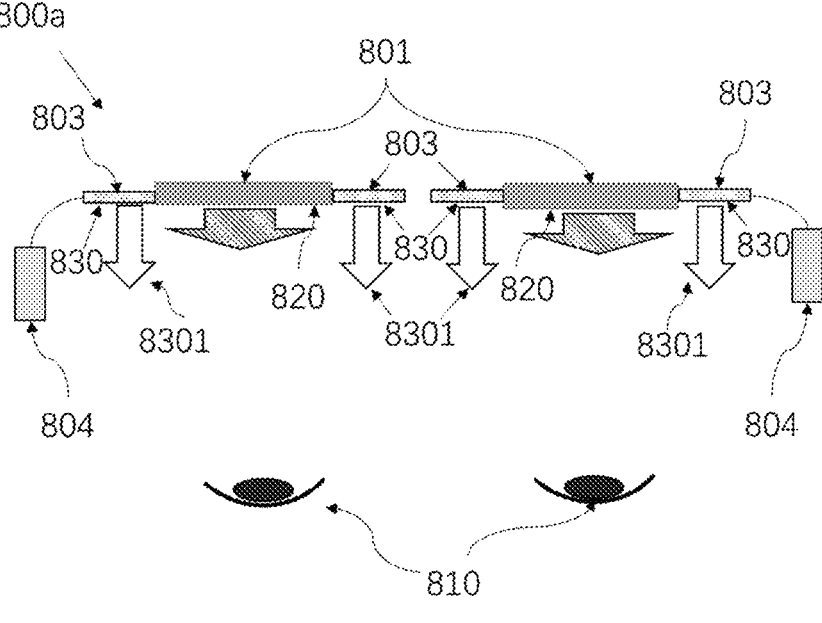
FIG. 8A is a schematic diagram of another wearable phototherapy display device.
Figure 8B:
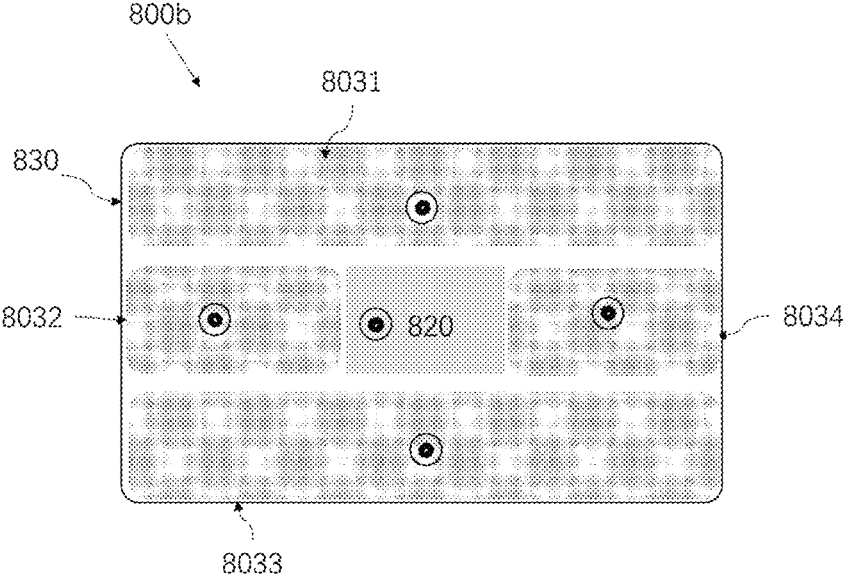
FIG. 8B is a schematic diagram of the relative area and positional relationship of projections of the light-emitting surface and the imaging plane in FIG. 8A on the same parallel plane.

The schematic diagram of another wearable phototherapy display device 800*a* is shown in FIG. 8A. The wearable phototherapy display device 800*a* includes micron display units 801, light sources 803, and drive devices 804. The wearable phototherapy display device performs imaging directly on the micron display units 801, and at this point, the imaging plane 820 is the display screen plane of each of the micron display units 801. The light source 803 is provided in the peripheral region of each of the micron display units 801 and includes light-emitting surfaces 830, and the light-emitting surfaces 830 are roughly parallel to a respective one of the imaging planes 820. At this point, the light emitted by the light source 803 (as shown by the arrow 8301 in FIG. 8A) is directed towards the periocular region of the human eye 810. Each light source 803 may further include a series of light-emitting sub-panels 8031, 8032, 8033, and 8034, as shown in FIG. 8B. These light-emitting sub-panels are integrated at the periphery of each of the micron display units 801, the light-emitting surface of each of these light-emitting sub-panels is roughly parallel to a respective one of the imaging planes 820, and the light emitted by the corresponding light source 803 is directed towards the skin at the periocular region, but not towards the human eye. In this manner, the imaging plane 820 does not substantially overlap with the light-emitting surface 830 of a respective one of the light sources 803. Each light source 803 is electrically connected to a respective one of the drive devices 804, and preferably, the drive device 804 can independently control the light-emitting sub-panels 8031 to 8034. It is to be noted that the drive device 804 can also provide driving for each of the micron display units 801. Similarly, preferably, a series of light-emitting sub-panels may have the same layout to reduce costs.

The wearable phototherapy display device provided by the present disclosure includes a display unit and a light source. The light source emits light having a peak wavelength between 400 nm and 1400 nm, and the emitted light is directed towards at least a part of the periocular region. The light source includes a light-emitting surface, and the display unit has an imaging plane. The included angle between the light-emitting surface and the imaging plane is less than 30 degrees, preferably, less than 10 degrees, and more preferably, equal to 0 degrees. The wearable phototherapy display device may include a micron display unit and in particular, may include optical waveguide lens. At this point, the micron display unit itself may be disposed on the side of the human face, and the images are transferred to the front of the human eye through the optical waveguide lens. The light source is preferably an OLED light source, may further include one or more OLED light-emitting panels or devices, preferably flexible panels or devices, to further reduce the weight and volume, and may be bent and cover the side of the face, such as the temple region. The OLED light source may also be made transparent and thus is suitable for integrating into AR glasses. The light source may be integrated on the side of the imaging plane away from the human eye and emits light towards the periocular region and the human eye. The light source may also be integrated on the side of the imaging plane close to the human eye, and at this point, preferably, the region where the light-emitting surface of the light source overlaps with the imaging plane does not emit light, but the light source only emits light at the periphery of the imaging plane; or the light source is integrated on the side of the imaging plane close to the human eye, but the overlapping region with the imaging plane adopts a transparent double-sided light-emitting structure or a single-sided light-emitting array layout. The light source may also be integrated in the peripheral region of the micron display unit, emits light only in the peripheral region of the imaging plane, and carries out phototherapy on the periocular region. Such a wearable phototherapy display device can simultaneously achieve the functions of display and phototherapy and allows people to receive phototherapy on the skin around the eyes or the eyes while watching movies, playing games or carrying out other virtual work. If deep red light and near-infrared light of the wavelength of 680 nm to 1000 nm are emitted, since such light is hardly perceived by human eyes, the normal use of the screen will not be affected. Of course, people can also choose to wear such a display device directly, instead of watching images or just watching some static or text-type images, and receive other treatments under the light of the wavelength of 400 nm to 700 nm, thereby achieving multiple purposes.

It is to be understood that various embodiments described herein are merely examples and are not intended to limit the scope of the present disclosure. Therefore, it is apparent to those skilled in the art that the present disclosure as claimed may include variations of specific embodiments and pre-ferred embodiments described herein. Many of the materials and structures described herein may be replaced with other materials and structures without departing from the spirit of the present disclosure. It is to be understood that various theories as to why the present disclosure works are not intended to be limitative.

What is claimed is:

1. A wearable phototherapy display device, comprising:
a display unit and a light source;

wherein the display unit has an imaging plane, said display unit adapted to display images on said imaging plane, and the imaging plane is disposed directly in front of a human eye;

the light source emits light having a peak wavelength between 680 nm and 1000 nm, and the light emitted by the light source is directed towards at least a part of a periocular region; and the light source comprises a light-emitting surface, and an included angle between the light-emitting surface and the imaging plane is less than 10 degrees;

a projection of the light-emitting surface of the light source and a projection of the imaging plane on the same parallel plane have an overlapping region; and the light source comprises an organic light-emitting diode (OLED) light source, the OLED light source comprises at least one OLED light-emitting panel;

whereby a user, during use of the wearable phototherapy display device, will be able to view images displayed by the display unit while receiving phototherapy.

2. The wearable phototherapy display device of claim 1, wherein the OLED light source comprises a plurality of OLED light-emitting panels.

3. The wearable phototherapy display device of claim 1, wherein the OLED light source is flexible.

4. The wearable phototherapy display device of claim 1, wherein the OLED light-emitting panel comprises a plural-ity of OLED devices, the plurality of OLED devices are spaced apart from each other such that a transmittance of the light source is greater than or equal to 30%.

5. The wearable phototherapy display device of claim 4, wherein the OLED light-emitting panel comprises a plural-ity of OLED devices, the plurality of OLED devices are spaced apart from each other such that a transmittance of the light source is greater than or equal to 50%.

6. The wearable phototherapy display device of claim 1, wherein the OLED light source comprises a top-emitting device, or a stacked device, or a double-sided light-emitting device.

7. The wearable phototherapy display device of claim 1, further comprising a drive device, wherein the drive device is electrically connected to the light source.

8. The wearable phototherapy display device of claim 7, wherein the drive device comprises any one or more of following components: a power supply, a charging device, a Bluetooth communication device, a chip, a lead, a circuit board or a switch.

9. The wearable phototherapy display device of claim 5, wherein the OLED light-emitting panel comprises a plural-ity of OLED devices, the plurality of OLED devices are spaced apart from each other such that a transmittance of the light source is greater than or equal to 70%.

10. The wearable phototherapy display device of claim 8, wherein the power supply comprises a battery.

11. The wearable phototherapy display device of claim 7, wherein the drive device is capable of being wirelessly connected to an external electronic device.

12. The wearable phototherapy display device of claim 11, wherein the external electronic device further comprises an application (APP), and the external electronic device is capable of controlling the light source on and off through the APP, or controlling the light source to adjust brightness of the light source through the APP.

13. The wearable phototherapy display device of claim 11, wherein the drive device comprises a Bluetooth com-munication device and is capable of being wirelessly connected to the external electronic device through the Bluetooth communication device.

14. The wearable phototherapy display device of claim 7, wherein the drive device independently drives at least two OLED light-emitting panels.

15. The wearable phototherapy display device of claim 7, wherein the display unit is electrically connected to the drive device.

16. The wearable phototherapy display device of claim 1, wherein the display unit is a micron display unit.

17. The wearable phototherapy display device of claim 16, wherein the micron display unit uses any one or more of an OLED, a micro LED or a laser as a display light source.

18. The wearable phototherapy display device of claim 1, further comprising an optical waveguide lens.

19. The wearable phototherapy display device of claim 1, wherein the overlapping region between the light-emitting surface of the light source and the imaging plane are configured not to emit light.

20. The wearable phototherapy display device of claim 1, wherein the periocular region comprises following regions and combinations of the following regions: a lower eye socket, an inner corner of an eye, an outer corner of an eye, an upper eyelid, a nasal bridge, a nasal root, a temporal region, a forehead, and a cheekbone.

21. The wearable phototherapy display device of claim 1, wherein the light source is disposed on a front side or a back side of the imaging plane.

22. The wearable phototherapy display device of claim 1, wherein the wearable phototherapy display device is a pair of virtual reality (VR) glasses, a pair of augmented reality (AR) glasses or a helmet with a display.

* * * * *